United States Patent [19]

Grimm et al.

[11] Patent Number: 4,618,707
[45] Date of Patent: Oct. 21, 1986

[54] PREPARATION OF MENTHANE DIISOCYANATE BY ADDITION OF ISOCYANIC ACID TO TERPINYL MONOISOCYANATES

[75] Inventors: Robert A. Grimm, Columbus; Jai H. Kyung, Dublin; Phyllis L. Brusky; Joseph G. Holehouse, both of Columbus; Biau-hung Chang, Worthington, all of Ohio

[73] Assignee: Ashland Oil, Inc., Ashland, Ky.

[21] Appl. No.: 801,443

[22] Filed: Nov. 25, 1985

[51] Int. Cl.[4] ............................................. C07C 71/00
[52] U.S. Cl. .................................................. 560/337
[58] Field of Search ..................... 260/453 P; 560/337

[56] References Cited

U.S. PATENT DOCUMENTS 3,290,350 12/1966 Hoover ............................. 260/453 P
3,471,542 10/1969 Cross et al. ...................... 260/453 P
4,377,530 3/1983 Trenbeath et al. ............... 260/453 P

FOREIGN PATENT DOCUMENTS 1243291 8/1971 United Kingdom ............ 260/453 P

Primary Examiner—Alan Siegel
Attorney, Agent, or Firm—John F. Jones

[57] ABSTRACT

A process for preparing menthane diisocyanate by reaction of a terpinyl monoisocyanate with isocyanic acid in a medium which is an excess of isocyanic acid, a polar solvent, or a mixture of solvents which includes a polar solvent in the presence of a catalyst which is a Bronsted acid or a Lewis acid is disclosed.

7 Claims, No Drawings

PREPARATION OF MENTHANE DIISOCYANATE BY ADDITION OF ISOCYANIC ACID TO TERPINYL MONOISOCYANATES

This invention relates to a novel process for the preparation of menthane diisocyanate from terpinyl monoisocyanates by the direct addition of isocyanic acid to the monoisocyanates in the presence of certain solvents and catalysts.

The addition of isocyanic acid to unsaturated terpene hydrocarbons such as alpha-pinene, beta-pinene and limonene in the presence of a hydrocarbon solvent such as toluene and in the presence of a boron trifluoride catalyst to form the terpinyl monoisocyanate has been disclosed by Lesiak and Forys, *Polish Journal of Chemistry*, 52, 927 (1978).

Menthane diisocyanates have been previously prepared by the phosgenation of the corresponding diamine as disclosed in U.S. Pat. No. 3,424,780 and by the reaction of the corresponding diformamide with t-butyl hypochlorite and subsequent decomposition as disclosed in U.S. Pat. No. 2,728,787 and by the base pyrolysis of dicarbamate of corresponding diamine as disclosed in U.S. Pat. No. 2,692,275.

The preparation of menthane diisocyanate by the addition of isocyanic acid to terpinyl monoisocyanates has not previously been disclosed.

Menthane diisocyanate (1,8-diisocyanato-p-menthane) is known to be a raw material for the production of polyurethanes. In contrast to many other commercial diisocyanates, menthane diisocyanate is neither lachrymatory nor malodorous having a boiling point of 74–75 degrees C. at 0.1–0.05 mm, 93–96 degrees C. at 0.4 mm, or 150 degrees C. at 9 mm. Because menthane diisocyanate is a tertiary isocyanate, it is less reactive in the formation of polyurethanes than the usual aromatic and primary aliphatic isocyanates. Menthane diisocyanate can be made more reactive in the polyurethane reaction by the use of suitable catalysts such as tin alkoxides as is well known in the art. Menthane diisocyanate is also known to be useful as a modifier in some other adhesives and plastics applications.

In order to prepare menthane diisocyanate from the usual raw materials such as pinene and limonene by the known methods, three or four steps are required which makes the menthane diisocyanate thus produced too costly for wide use in polyurethane applications.

Thus, it is an object of this invention to provide an improved and less costly process for the production of menthane diisocyanate in a single step from terpinyl monoisocyanates by the direct addition of isocyanic acid thereto.

We have discovered an improved process for the production of menthane diisocyanate which comprises the reaction of a terpinyl monoisocyanate, such as alpha-terpinyl monoisocyanate, with isocyanic acid in the presence of a polar solvent or a mixture of solvents which includes a polar solvent and in the presence of a catalyst which is a Bronsted or Lewis acid at a temperature in the range of from about −25 degrees C. to about 100 degrees C. and at a pressure in the range of from about atmospheric to about 2000 psi.

The terpinyl monoisocyanates can exist in several isomeric forms, but for the sake of simplicity the terpinyl monoisocyanates useful in this invention will include those which conform to the following general formula:

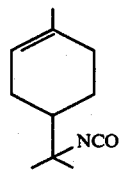

Similarly, the menthane diisocyanates produced by the process of this invention include those which conform to the following general formula:

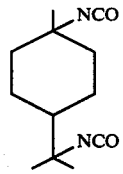

In the practice of this invention the choice of solvent is an important factor affecting the process of converting a terpinyl monoisocyanate to menthane diisocyanate by the reaction with isocyanic acid. Polar solvents or mixed solvents which include a polar solvent are preferred in the process of this invention. Nitrohydrocarbon solvents such as nitromethane, nitroethane, nitrobenzene and nitropropanes (1-nitro propane and 2-nitropropane) and solvent systems which include one or more of these solvents usually give the best yields of menthane diisocyanate. The chlorinated and nitrile solvents are marginally effective. Other polar solvents, such as acetone and glyme, are not effective because they are believed to form extensive hydrogen-bonding with isocyanic acid (HNCO) which results in excessive stabilization for the HNCO molecule. Nitrogen-containing polar solvents such as dimethyl formamide (DMF) are unsuitable for use in the process of this invention.

Organic carbonate solvents such as propylene carbonate, ethylene carbonate, dimethyl carbonate and diethyl carbonate which are much less toxic than nitrohydrocarbons have also been found to be good solvents for the addition of HNCO to terpinyl monoisocyanates to form menthane diisocyanates in accordance with this invention. Among these organic carbonate solvents propylene carbonate is particularly preferred.

Some mixed solvents such as mixtures of propylene carbonate and toluene and mixtures of one or more organic carbonates with solvents such as xylene, toluene, benzene, chlorobenzene, dichlorobenzene, methylnaphthalene, and nitro hydrocarbons can be used effectively as solvents in the process of this invention. The process of this invention can be run at temperatures below 0 degrees C. using excess liquid HNCO as solvent. For instance, the reaction of alpha-terpinyl isocyanate with an excess of HNCO using $CF_3SO_3H$ as catalyst at −20 degrees C. for 2 hours gave a 16% yield of menthane diisocyanate with a selectivity of 80%.

Catalysts which can be used in the process of this invention include acids which are commonly known as Bronsted and Lewis acids. Among the specific acid catalysts which can be employed in the process of this invention include perfluorinated sulfonic acids ($CF_3SO_3H$ pentafluoroethane sulfonic acid, nonafluorobutane sulfonic acid, perfluoro octane sulfonic acid, and the like), boron trifluoride, boron trifluoride etherate, toluene sulfonic acid, benzene sulfonic acid, camphor sulfonic acid, naphthalene sulfonic acid, methane sulfonic acid, aluminum trichloride, and iodine. The most effective catalysts are the perfluorinated sulfonic acids and boron trifluoride catalysts. The catalysts are effective when used in from about 1 to 20 mole% based on the monoisocyanate and are most effective when used in from about 10 to 15 mole%.

In the process of this invention the mole ratio of HNCO to the monoisocyanate should be in the range of from about 5:1 to about 30:1, respectively and preferably from about 10 to 30 in order to obtain the best yields.

The process of this invention is further illustrated in the following representative examples.

EXAMPLE 1

In a 5 ml glass vial equipped with efficient magnetic stirrer, 0.1 g of alpha-terpinyl monoisocyanate was dissolved in 2 ml of nitromethane. To this mixture was added 0.5 ml of clear liquid isocyanic acid. The resulting mixture was stirred well and 2–5 drops of trifluoromethane sulfonic acid was added. The reaction vial was closed and the mixture was stirred for 2 hours at room temperature. The solid cyanuric acid was removed from the reaction mixture at this point by filtration and the filtrate was analyzed by gas chromatography and 0.036 g of alpha terpinyl monoisocyanate and 0.061 g of menthane diisocyanate (1.8-diisocyanato-p-methane) were found to be present. This represents a conversion of 70% of the terpinyl monoisocyanate, a selectivity of 67% to the menthane diisocyanate and an overall yield of 47% of the diisocyanate.

EXAMPLE 2

In a 5 ml glass vial equipped with magnetic stirrer 0.1 g of alpha terpinyl monoisocyanate was placed and cooled to −20 degrees C. Then 2.0 ml of clear liquid isocyanic acid was added to the vial along with 5 drops of trifluoromethane sulfonic acid. The reaction vial was closed and the mixture was stirred for 2 hours at −20 degrees C. At this point 2 ml of toluene was added to the reaction mixture and the resulting mixture was warmed to room temperature with continued stirring. The diisocyanate product was recovered and analyzed as in Example 1. A 20% conversion with 80% selectivity to menthane diisocyanate were obtained.

EXAMPLE 3

The procedure of Example 1 was followed using the solvents shown in Table 1 in place of nitromethane. The results obtained are given in Table 1.

TABLE 1

| Solvent | % Conversion | % Selectivity | % Yield |
| --- | --- | --- | --- |
| nitromethane | 70 | 67 | 47 |
| nitrobenzene | 76 | 52 | 40 |
| nitroethane | 49 | 58 | 28 |
| toluene | None | — | — |
| chlorobenzene | 22 | 11 | 5.4 |
| o-dichlorobenzene | 14 | 14 | 2.0 |

EXAMPLE 4

The procedure of Example 1 was followed using the catalysts shown in Table 2 in place of the trifluoromethane sulfonic acid. The results obtained are given in Table 2.

TABLE 2

| Catalyst | % Conversion | % Selectivity | % Yield |
| --- | --- | --- | --- |
| $CF_3SO_3H$ | 76 | 52 | 40 |
| $I_2$ | 55 | 33 | 18 |
| $AlCl_3$ | 87 | 11 | 10 |
| TsOH | 29 | 33 | 10 |
| $CH_3SO_3H$ | 46 | 15 | 7 |
| camphor sulfonic acid | 10 | 7 | 1 |
| $BF_3$ etherate | 7 | 80 | 6 |

EXAMPLE 5

The procedure of Example 1 was followed using 0.05 g of boron trifluoride etherate catalyst in place of the trifluoromethane sulfonic acid and the various solvents listed in Table 3. The results obtained in these experiments are given in Table 3.

TABLE 3

| Solvent | % Conversion | % Selectivity | % Yield |
| --- | --- | --- | --- |
| propylene carbonate | 42 | 48 | 20 |
| nitromethane | 30 | 51 | 15 |
| toluene/propylene carbonate 1:1 | 41 | 47 | 19 |

EXAMPLE 6

The procedure of Example 1 was followed using 0.10 g of the terpinyl monoisocyanate, 0.5 ml of HNCO, 0.5 ml of propylene carbonate and 0.060 g of $BF_3$ etherate to give a 73% conversion of the monoisocyanate with a 50% selectivity to and 37% yield of the menthane diisocyanate.

We claim:

1. The process for preparing menthane diisocyanate consisting essentially of reacting a terpinyl monoisocyanate with isocyanic acid at a pressure in the range of from about atmospheric to about 2000 psi in a medium which is selected from the group consisting of a nitrohydrocarbon, an organic carbonate, and a mixture of an organic carbonate with toluene, benzene, xylene or chlorobenzene in the presence of a catalyst which is at least one member selected from the group consisting of a perfluorinated sulfonic acid, boron trifluoride, boron trifluoride etherate, toluene sulfonic acid, benzene sulfonic acid, camphor sulfonic acid, naphthalene sulfonic acid, methane sulfonic acid, aluminum chloride, and iodine.

2. The process of claim 1 wherein the nitro hydrocarbon is nitromethane, nitroethane, a nitropropane or nitrobenzene.

3. The process of claim 2 wherein the organic carbonate is ethylene carbonate, propylene carbonate, dimethyl carbonate, diethyl carbonate or ethylene carbonate.

4. The process of claim 1 wherein the catalyst is present in from about 1 to 20 mole% based on the terpinyl monoisocyanate.

5. The process of claim 4 wherein the mole ratio of the isocyanic acid to the terpinyl monoisocyanate is in the range of from about 5:1 to about 30:1, respectively.

6. The process of claim 5 wherein the medium is nitromethane and the catalyst is trifluoromethane sulfonic acid.

7. The process of claim 6 wherein the medium is an excess of isocyanic acid and the catalyst is trifluoromethane sulfonic acid.

* * * * *